US006760100B2

United States Patent
Ivakhnenko et al.

(12) United States Patent
(10) Patent No.: US 6,760,100 B2
(45) Date of Patent: *Jul. 6, 2004

(54) METHOD AND APPARATUS FOR CLASSIFYING DEFECTS OCCURRING AT OR NEAR A SURFACE OF A SMOOTH SUBSTRATE

(75) Inventors: Vladimir I. Ivakhnenko, Norwood, MA (US); John C. Stover, North Attleboro, MA (US)

(73) Assignee: ADE Corporation, Westwood, MA (US)

( * ) Notice: Subject to any disclaimer, the term of this patent is extended or adjusted under 35 U.S.C. 154(b) by 178 days.

This patent is subject to a terminal disclaimer.

(21) Appl. No.: 09/804,218

(22) Filed: Mar. 12, 2001

(65) Prior Publication Data

US 2002/0154295 A1 Oct. 24, 2002

(51) Int. Cl.[7] ............................................... G01N 21/00
(52) U.S. Cl. ............................... 356/237.2; 356/237.3; 356/327.4
(58) Field of Search .......................... 356/237.2–237.5; 702/35, 81.84

(56) References Cited

U.S. PATENT DOCUMENTS

| | | | |
|---|---|---|---|
| 4,893,932 A | | 1/1990 | Knollenberg |
| 5,037,202 A | | 8/1991 | Batchelder et al. |
| 5,046,847 A | | 9/1991 | Nakata et al. |
| 5,363,187 A | | 11/1994 | Hagiwara et al. |
| 5,436,464 A | | 7/1995 | Hayano et al. |
| 5,471,298 A | | 11/1995 | Moriya |
| 5,515,163 A | | 5/1996 | Kupershmidt et al. |
| 5,539,752 A | * | 7/1996 | Berezin et al. ............ 702/35 |
| 5,712,701 A | | 1/1998 | Clementi et al. |
| 5,761,064 A | * | 6/1998 | La et al. .................... 702/35 |
| 5,883,710 A | | 3/1999 | Nikoonahad et al. |
| 5,903,342 A | | 5/1999 | Yatsugake et al. |
| 6,314,379 B1 | * | 11/2001 | Hu et al. ................... 702/35 |
| 2002/0035435 A1 | * | 3/2002 | Ninomiya et al. ......... 702/35 |

OTHER PUBLICATIONS

Katsumi Takami; Defect Inspection of Wafers by Laser Scattering; Feb. 1, 1997; pp. 181–187; vol. 44, No. 1–3; Materials Science and Engineering B, Elsevier Sequoia, Lausanne, China.

F. Passek et al; Discrimination of Particles and Defects on Silicon Wafers; Jul. 1999; pp. 191–196; vol. 45, No. 2–3; Microelectronic Engineering, Elsevier Publishers BV., Amsterdam, The Netherlands.

* cited by examiner

Primary Examiner—Michael G. Lee
Assistant Examiner—Ahshik Kim
(74) Attorney, Agent, or Firm—Alston & Bird LLP

(57) ABSTRACT

In an optical inspection system, defects such as particles, pits, subsurface voids, mounds, or other defects occurring at or near the smooth surface of a substrate are classified by type and size based on the magnitude S of a signal produced by collected light for each of a plurality N of different test configurations, yielding a plurality of signal magnitudes $S_1$ through $S_N$. A database is consulted, comprising a relationship of S versus defect size d for each test configuration and for each of a plurality of idealized defect types, so as to determine a defect size d corresponding to each measured signal magnitude S, and an average defect size is determined for each defect type. Signal magnitudes $<S_1>$ through $<S_N>$ that would be produced by a defect of the average size are determined for each defect type, and defect type is determined based on a smallest deviation between the measured magnitudes and the determined magnitudes.

41 Claims, 4 Drawing Sheets

METHOD AND APPARATUS FOR CLASSIFYING DEFECTS OCCURRING AT OR NEAR A SURFACE OF A SMOOTH SUBSTRATE

FIELD OF THE INVENTION

The present invention relates to methods and apparatus for optically detecting defects in or on a smooth surface of a substrate such as a silicon wafer, and for classifying the defects in terms of defect type and size.

BACKGROUND OF THE INVENTION

Optical inspection methods are frequently used for inspecting the quality of a smooth surface of a substrate such as a silicon wafer, computer disk, or the like. In most such inspection systems, the surface is impinged with a beam of laser light and the light scattered and reflected from the surface is collected and converted into electrical signals that are analyzed so as to infer the presence and size of certain defects on the surface. At least in the case of optical inspection of silicon wafers that are used as the starting material for making integrated circuit chips, the types of defects of major concern include particles of foreign materials on the surface, pits formed in the surface, scratches in the surface, and others.

Particles on the wafer surface can interfere with the lithography process by which lines of electrically conductive material are formed on the surface. As a general rule, any particle whose diameter is larger than half the width of the electrical lines to be laid onto the surface constitutes an unacceptable defect. If there are too many such particles, the wafer must be rejected. Currently, integrated circuits are being made with line widths as small as 0.25 µm (250 nm), so that particles larger than 125 nm in diameter occurring on the wafer surface would be cause for rejecting the wafer, while particles smaller than 125 nm would be tolerable. The semiconductor industry is quickly moving towards production of circuits composed of 0.18 µm and then 0.15 µm lines, which means that much smaller particles will soon cause concern.

Wafer inspection systems must be calibrated in order to function properly to accurately determine the diameter of a particle. The calibration is typically done by intentionally placing a plurality of particles of various known diameters on the wafer surface and inspecting the wafer with the inspection apparatus, so that the scattered light intensities produced from the various sizes of particles can be correlated to the particle sizes. These calibration particles are usually spheres made of polystyrene latex (PSL).

One difficulty that has been encountered in wafer inspection processes is that identically sized particles of different material types can produce substantially different scattered light intensities. Stated differently, two particles made of different materials and having substantially different diameters may produce virtually the same measured scattered light intensity. For example, it has been found that silicon particles of a given diameter will produce a much larger scatter intensity than the same diameter PSL particle. In fact, among the various types of materials that can commonly appear on a wafer surface in the form of particles, PSL particles tend to be one of the lowest sources of light scattering. Thus, after the inspection apparatus has been calibrated with PSL particles, the apparatus will tend to overestimate the diameters of silicon particles and those of many other materials. Accordingly, wafers are rejected as having particles larger than half the line width, even though in reality the particles may be smaller than half the line width. Therefore, the accuracy with which particles can be sized by light scattering can be greatly increased if something is known about the particle material.

Another advantage to the semiconductor industry in being able to identify particle material is that this information provides a strong clue as to the source of the contamination. Because particle contamination has to be reduced to a level where useful product can be produced, finding and eliminating contamination sources quickly is economically important.

For light of a given wavelength, every material has an index of refraction, which indicates how much the speed of light is reduced within the material, and an absorption coefficient, which is generally indicative of how opaque the material is to the light. The combination of the index of refraction and absorption coefficient, which are known as the material constants, is unique for each different material. The combinations of these material constants can be roughly separated into four groups: (1) dielectrics such as PSL, $SiO_2$, and $Al_2O_3$ (low index of refraction and zero absorption coefficient); (2) semiconductors such as silicon (large index of refraction and small absorption coefficient); (3) gray metals such as tungsten (large index of refraction and large absorption coefficient); and (4) good conductors such as silver (small index of refraction and large absorption coefficient).

The combination of particle material, along with particle shape and the material constants for the substrate surface (which are known), completely and uniquely define the pattern of light scattered by the particle for any given light source. Moreover, for particles whose average diameter is less than about one-fifth of a wavelength of the illuminating light, the particle shape does not play a significant role in determining the scatter pattern. Thus, for visible light and particles smaller than about 100 nm, knowledge of the average particle diameter and the various material constants are enough to calculate the scatter pattern for a given scattering geometry. This fact has allowed the development of scattering models that predict scatter patterns for a given set of conditions. These models have been experimentally confirmed and the results published.

What would be desirable is a system and method for solving the more difficult inverse problem. That is, it would be desirable to be able to determine the particle material and average particle diameter from a knowledge of the scatter pattern. Heretofore, methods have been developed for determining average particle diameter by analyzing the scatter pattern, for example as described in commonly owned U.S. Pat. No. 5,712,701, which is hereby incorporated herein by reference. However, as noted above, the accuracy of such methods depends on the calibration of the system, and currently the calibration must be performed using PSL spheres, which have substantially different material constants from some of the other materials that can appear as particles on a wafer.

Methods for identifying particle material have been proposed. For instance, U.S. Pat. No. 5,037,202 to Batchelder et al. discloses methods and apparatus in which two parallel light beams that are initially mutually coherent but of different polarizations are focused onto a focal plane (such as the surface of a wafer) such that they are displaced apart from each other at the focal plane. After the beams are reflected from the surface, a further optical system intercepts the beams and combines them so that a particle-induced phase shift in one of the beams is manifested by a change in the elliptical polarization of the combined beams. A first detector is responsive to the combined beam's intensity along a first polarization axis to produce a first output, and a second detector is responsive to the combined beam's intensity along a second polarization axis to produce a second output. The first and second outputs are added to provide an extinction signal and are subtracted to provide a phase shift signal. The phase shift and extinction are correlated with index of refraction of the particle material, and hence the identity of the material purportedly can be determined based on the phase shift and extinction values. The size of the particle purportedly can be inferred from its position on a curve of extinction versus phase shift. Thus, in Batchelder's system and method, information about the particle is inferred by analyzing the specularly reflected beams. A disadvantage of this approach is that the reflected light is relatively insensitive to changes in particle properties, such that small particles (e.g., particles on the order of 100 nm or smaller) will produce quite small changes in the specularly reflected beams that can be difficult to accurately measure. Accordingly, the Batchelder approach may not be optimum for identifying small particles of the size that begin to cause problems in integrated circuit manufacturing.

U.S. Pat. No. 5,515,163 to Kupershmidt et al. discloses methods and apparatus in which a polarized laser beam is intensity modulated at a first frequency and is split into two orthogonally polarized beams, and the two beams are phase shifted relative to each other at a second frequency. The two phase-shifted beams are directed onto the surface being inspected, and light scattered by particles at an angle to the two beams is detected. The detected light is synchronously demodulated to determine the amplitude of the scattered light at the frequency of intensity modulation and the amplitude and phase of the scattered light at the frequency of phase modulation. These quantities purportedly can be correlated to size and refraction index of particles to permit identification of particles. Kupershmidt's method involves complicated calculations, and the measurements require sampling over a number of modulation cycles in order to obtain accurate measurements for a given scanned portion of the surface being inspected. Accordingly, scanning of the entire surface would likely be relatively slow.

The assignee of the present application has developed a method and apparatus for identifying the material of which a particle is made, as described in commonly assigned U.S. Pat. No. 6,122,047, the entire disclosure of which is incorporated herein by reference. The method involves measuring the scatter pattern produced by light scattering from a particle, and comparing the measured scatter pattern with a plurality of predetermined scatter patterns produced by particles of various known materials and sizes, so as to identify the predetermined scatter pattern that most nearly matches the measured one. The scatter pattern is defined by signals from a plurality of light collectors positioned in different locations with respect to the particle and incident light beam.

SUMMARY OF THE INVENTION

The present invention represents an improvement over the method and apparatus disclosed in U.S. Pat. No. 6,122,047, and is applicable not only for identifying particle material and size, but also for identifying and sizing other types of defects such as pits, scratches, subsurface defects (e.g., voids), etc. In accordance with the invention, a preferred method for classifying defects occurring at or near a surface of a smooth substrate proceeds as follows:

(a) The method begins by defining a plurality M of different idealized types of defects, labeled m=1 to M (e.g., spherical particle, conical pit, etc.), that can occur at the surface of the substrate, such that a given defect occurring at the surface can be categorized into one of the M defect types and can be described in terms of size, at least approximately, by a size parameter $d_m$.

(b) Next, for each of the M different idealized types of defects, a database is constructed containing a plurality N of different sets of data, labeled n=1 to N. Each set of data comprises a relationship between a magnitude S of a signal from a light collector versus size parameter. The N different sets of data for each defect type correspond to N different predetermined test configurations in which a beam of light having predetermined characteristics is impinged on the surface of the substrate at a predetermined incident angle and light emanating from the surface is collected by the light collector at a predetermined location above the surface and the intensity of the collected light is measured. Each of the N different test configurations differs from each of the other configurations in some respect that produces an independent relationship between a signal magnitude and a defect size. The N different predetermined test configurations are the same for each idealized defect type. Thus, there are M different databases each containing N different sets of data. For example, if the defect types comprise spherical particles, conical pits, ellipsoidal particles, and mounds (i.e., M=4), and there are three different test configurations represented by three light collectors located in different locations above the substrate surface (i.e., N=3), there would be four different databases each containing three data sets of signal magnitude versus defect size.

(c) The substrate is tested with each of the N different predetermined test configurations so as to derive N signal magnitudes $S_1, \ldots, S_N$ for a defect to be sized and classified.

(d) Each of the M different databases is consulted to determine a defect size d corresponding to each of the N measured signal magnitudes $S_1, \ldots, S_N$. Thus, N different sizes $d_1$ to $d_N$ are determined for each of the M different idealized defect types.

(e) For each of the M different defect types, an average size <d> is calculated based on the N different sizes $d_1$ to $d_N$, and based on this average size <d>, the respective database is used to determine the signal magnitudes that would be produced by the respective defect type having the size <d>. These signal magnitudes are denoted $<S_1>$ to $<S_N>$. In general, these signal magnitudes will differ from one another, with the degree of variance between them being generally indicative of how closely the defect being analyzed resembles the respective idealized defect type.

(f) Thus, for each idealized defect type, a deviation parameter σ is calculated representing a combined deviation between the measured signal magnitudes $S_1$ to $S_N$ and the determined signal magnitudes $<S_1>$ to $<S_N>$, so as to derive a plurality of deviation parameters $\sigma_1$ to $\sigma_M$ corresponding to the M different idealized defect types.

(g) The defect being analyzed is classified as being of the idealized type having the smallest deviation parameter σ. The size of the defect is determined based on the average size <d> corresponding to that idealized type.

In an alternative method in accordance with the invention, steps (a) through (d) above are performed, and the defect is classified as being of the idealized type having the smallest spread between the plurality of sizes $d_1$ to $d_N$. The size of the defect is determined based on an average of the sizes $d_1$ to $d_N$.

The plurality N of test configurations can be provided in various ways. In one embodiment, a plurality of light collectors are positioned above the surface of the substrate for collecting light scattered to various regions of the space of the surface. Thus, the plurality of test configurations are effected simultaneously when a single light beam is impinged on a given point of the substrate surface.

Alternatively, the plurality of test configurations can be effected by changing a property of the incident light beam or a property of the scattered light received at a light collector. For instance, the incident angle of the light beam can be varied to produce the plurality of test configurations, or the polarization of the incident beam can be varied. Another possibility is to vary the polarization of the light received at the light collector. The method used for effecting the plurality of test configurations is not critical, as long as the different configurations produce discernable differences in the characteristics of the light that rebounds from the substrate surface and defect so that such differences can be correlated with defect type and size.

A significant advantage of the present invention is that the method does not depend on using any particular scanner configuration, but rather can be adapted to any configuration simply by constructing the databases in accordance with the scanner configuration. The databases can be provided either analytically based on mathematical models, or empirically by testing known defect types and sizes.

Furthermore, the invention is not negatively affected by the well-known phenomenon of "dips" in the scatter distribution (i.e., scattered light intensity versus scattering angle or equivalent) that are produced by certain types of defects, particularly silicon particles. In fact, the presence of these dips in the data actually enhances the ability to identify defect type because not all defect types exhibit such dips, and those that do exhibit dips have different dip characteristics. At any rate, because of the dip phenomenon, the signal magnitude S from a given light collector, when plotted against particle diameter d, can yield more than one diameter for a given signal magnitude. This presents no problem with the present invention, however; for any S versus d relationship in the database that has more than one size parameter d for a given signal magnitude S, each size parameter d corresponding to the signal magnitude S is simply treated as if it were from an additional test configuration. Thus, a deviation parameter $\sigma$ is calculated based on each of the diameters and is compared to the other deviation parameters to determine the smallest deviation parameter.

The average diameter $<d>$ for each idealized defect type in the database is preferably calculated as follows:

$$<d> = \frac{(S_1)^\alpha d_1 + (S_2)^\alpha d_2 + \ldots + (S_N)^\alpha d_N}{(S_1)^\alpha + (S_2)^\alpha + \ldots + (S_N)^\alpha}$$

The parameter $\alpha$ is a constant. Using different values for $\alpha$ allows the average size to be calculated in different ways. If $\alpha=0$ is chosen, then the average size $<d>$ is just the simple arithmetic average; however, using $\alpha=1$ is a more preferred approach that has yielded better accuracy for a number of defect types.

The deviation parameter for each defect type preferably is calculated based on a summation of differences between each measured signal magnitude S and the corresponding determined signal magnitude $<S>$ that corresponds to the average defect size $<d>$. For instance, the deviation parameter $\sigma$ can be calculated based on the formula:

$$\sigma = [|(<S_1> - S_1)|^\beta + |(<S_2> - S_2)|^\beta + \ldots + |(<S_N> - S_N)|^\beta]^{\frac{1}{\beta}}$$

The parameter $\beta$ is a constant. Using different values for $\beta$ allows the deviation parameter to be found in different ways. If $\beta=1$ is chosen, then the deviation parameter is the sum of the absolute values of the differences between the signals that were measured and the signals associated with the average size parameter $<d>$. A preferred value for $\beta$, however, is 2, such that the deviation parameter is the square root of the sum of the squares of the differences. This approach has yielded better accuracy for a number of defect types. Of course, it will be recognized that there are other ways in which a deviation parameter could be calculated in accordance with the invention, and the invention is not limited to any particular formula.

Once the deviation parameters $\sigma_1$ to $\sigma_M$ corresponding to the M different idealized defect types have been calculated, preferably, several of the smallest deviation parameters are identified and, for each of these deviation parameters, a relative probability value P is calculated, representing a relative probability that the defect in question belongs to the defect type associated with the particular deviation parameter. For example, if the three smallest deviation parameters are denoted $\sigma_1$, $\sigma_2$, and $\sigma_3$, a probability value for $\sigma_1$ is calculated based on the formula:

$$P_1 = \frac{(1/\sigma_1)^\delta}{(1/\sigma_1)^\delta + (1/\sigma_2)^\delta + (1/\sigma_3)^\delta}$$

Probability parameters $P_2$ and $P_3$ would be calculated by analogous formulas. The parameter $\delta$ is a constant. Using different values for $\delta$ allows the relative probability to be found in different ways. It has been found for many defect types that $\delta=1$ works well. However, other values for $\delta$ can be used instead, and indeed an entirely different formula could be used for deriving a probability parameter in accordance with the invention. Preferably, for each defect type corresponding to the three smallest deviation parameters, the defect type, probability value, and defect size are reported.

The invention also provides an apparatus for classifying defects in terms of type and size. The apparatus includes a storage medium storing the databases of signal magnitude versus size for each test configuration and defect type, a light collector system for collecting light that is scattered and/or reflected from the substrate and any defect thereon, and a computer connected with the light collector system and storage medium and operable to receive signals from the light collector system and access the databases to determine the defect type and size present on the substrate surface. Preferably, the apparatus includes a scanning system for effecting relative movement between the substrate being inspected and the incident light beam so that the beam is scanned over the entire substrate surface.

BRIEF DESCRIPTION OF THE DRAWINGS

The above and other objects, features, and advantages of the invention will become more apparent from the following description of certain preferred embodiments thereof, when taken in conjunction with the accompanying drawings in which.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
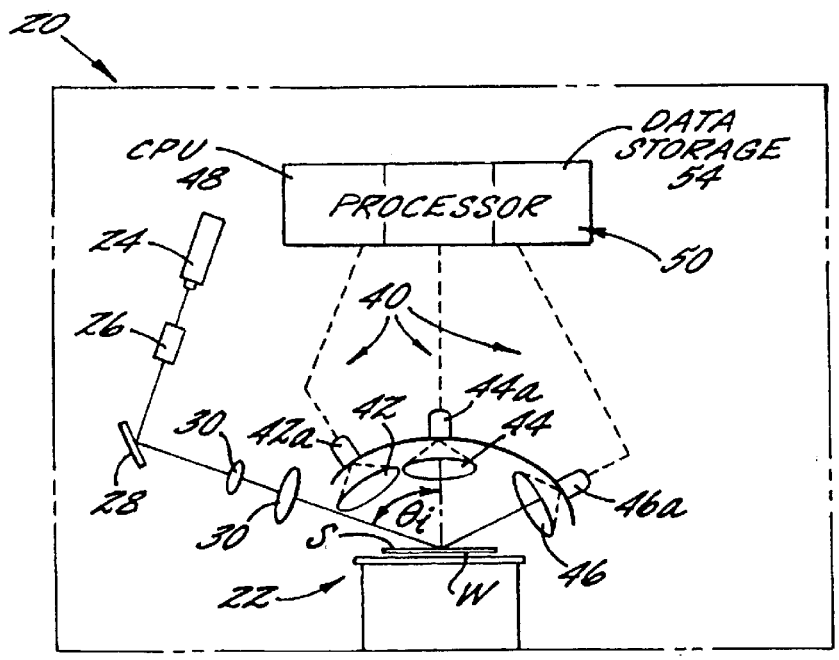
FIG. 1 is a schematic side elevation of an apparatus in accordance with one embodiment of the invention.
Figure 2:
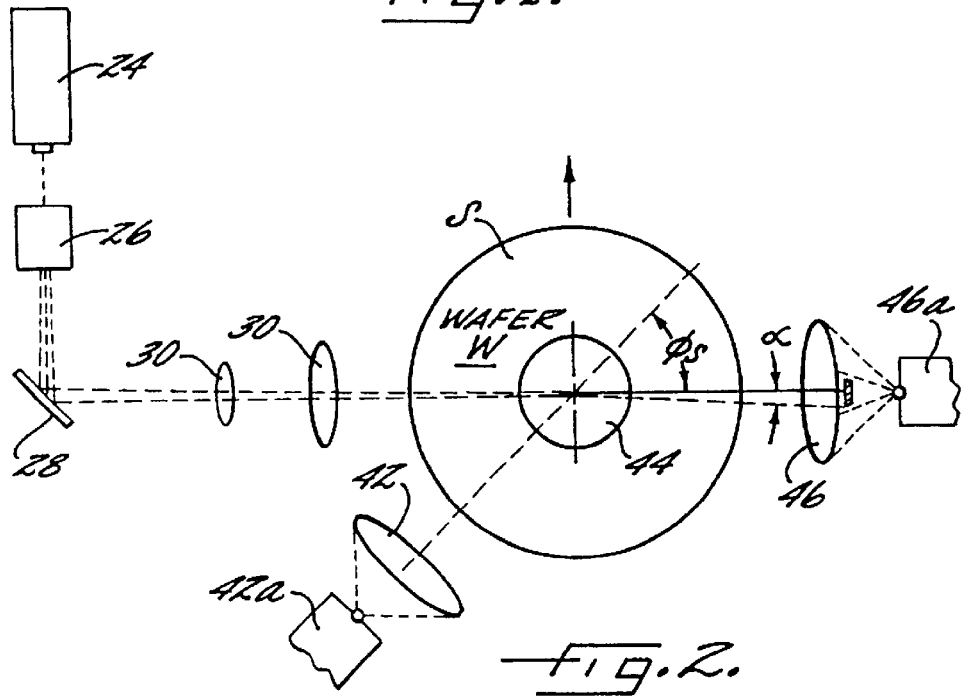
FIG. 2 is a schematic top plan view of the apparatus.

With reference to FIGS. 1 and 2, an apparatus 20 in accordance with a preferred embodiment of the invention is shown. The apparatus 20 includes a wafer transport device 22 adapted to support a substrate or wafer W to be inspected. For purposes of the present description, it is assumed that the wafer W is supported such that the surface S to be inspected is horizontal; however, it will be understood that the wafer need not be oriented horizontally. The apparatus 20 includes a light source 24 operable for creating a narrow beam of light. The light source 24 preferably is a laser emitting a light beam in the visible spectrum. Shorter wavelengths tend to produce larger particle scatter signals and thus contribute toward improved accuracy of measurement, while longer wavelengths tend to increase the maximum particle diameter for which the material can be identified and thus extend the particle-diameter range over which the method and apparatus are effective. The emitted beam can be passed through a beam expander 26 if desired, and then the beam is directed with the aid of one or more mirrors such as the mirror 28 and/or one or more lenses such as the lenses 30 such that the beam is impinged on the surface S of the wafer at an oblique angle of incidence $2_i$ measured from a surface normal that passes through the region of the surface S illuminated by the incident beam. Preferably, the incident angle $2_i$ is fairly large, for example about 45° to 80°, in order to emphasize the differences in scatter intensities for different locations in the hemispherical space above the surface S, as further described below.

The incident beam strikes the surface S at the incident angle $2_i$ and is specularly reflected therefrom and is also scattered in many directions by imperfections on the surface. A plane of incidence is defined by the incident beam and the surface normal. When the incident beam strikes a particle on the surface, the scattered light is scattered out of the plane of incidence.

In accordance with the present invention, the scattered light is collected by a plurality of collectors and analyzed in order to determine the type and size of defect occurring at the surface S. The specularly reflected light can also be collected and analyzed, if desired, depending on the types of defects to be classified. Thus, the apparatus in accordance with the invention includes a light collection system 40 for collecting scattered light at each of a plurality of locations spaced above the substrate surface. More particularly, a back collector 42 is located in a back region of the space above the surface S for collecting light scattered in a backward direction. As shown in FIG. 2, the back collector 42 can be displaced from the plane of incidence at a polar angle $N_s$ if desired. A center collector 44 is located in a center region of the space above the surface S proximate the surface normal. A forward collector 46 is located in a forward region of the space proximate the specularly reflected beam. The collectors 42, 44, 46 are formed by lenses and/or mirrors that collect scattered light and focus the collected light onto a corresponding detector 42a, 44a, 46a each of which produces a signal indicative of the intensity of the scattered light collected and focused onto the detector.

Each of the collectors 42, 44, 46 extends over a range of scatter angles $2_s$ and preferably is generally circular, although other collector shapes can be used. The lenses or mirrors of the collectors effectively integrate the collected scattered light such that the magnitudes of the signals produced by the corresponding detectors represent integrations of the light scattered over the areas of the collectors.

Each collector thus provides a separate signal that can indicate the presence of a defect at the portion of the surface impinged by the incident light beam. The apparatus 20 preferably includes a separate channel for each light collector, by which the signals are fed to and processed by a processor 50. The processor 50 includes a computer or CPU 48 and a data storage unit 54. In accordance with the invention, the data storage unit 54 stores a database containing information correlating the signal magnitudes S from each collector of the light collection system 40 with a size parameter d of a defect for each of a plurality of predetermined idealized defect types that can occur at the surface of the substrate.

Figure 3:
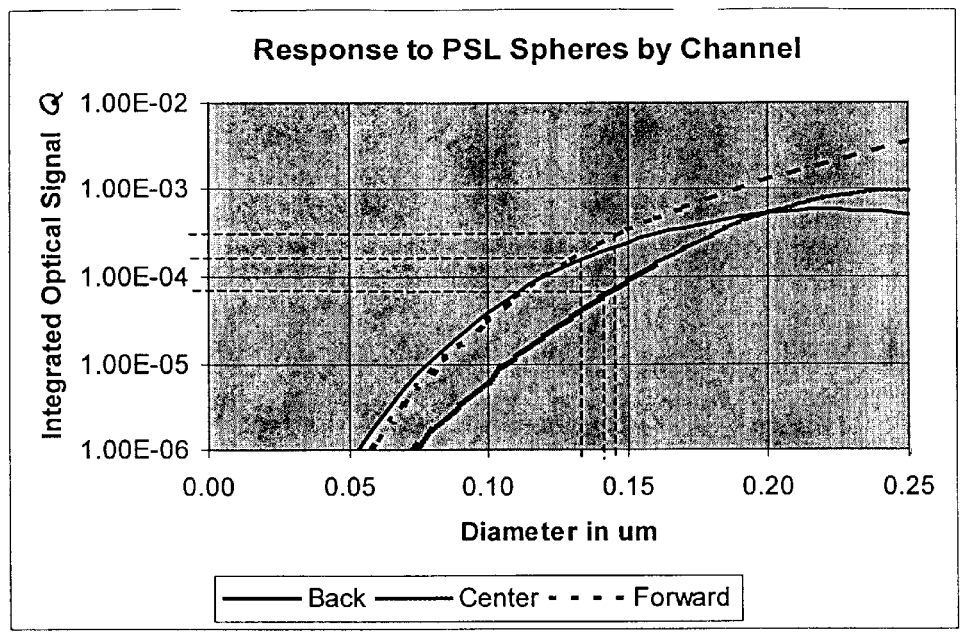
FIG. 3 is a plot of the integrated signal magnitude from each of the light detectors versus particle diameter for spherical polystyrene latex (PSL) particles on the substrate surface.
Figure 4:
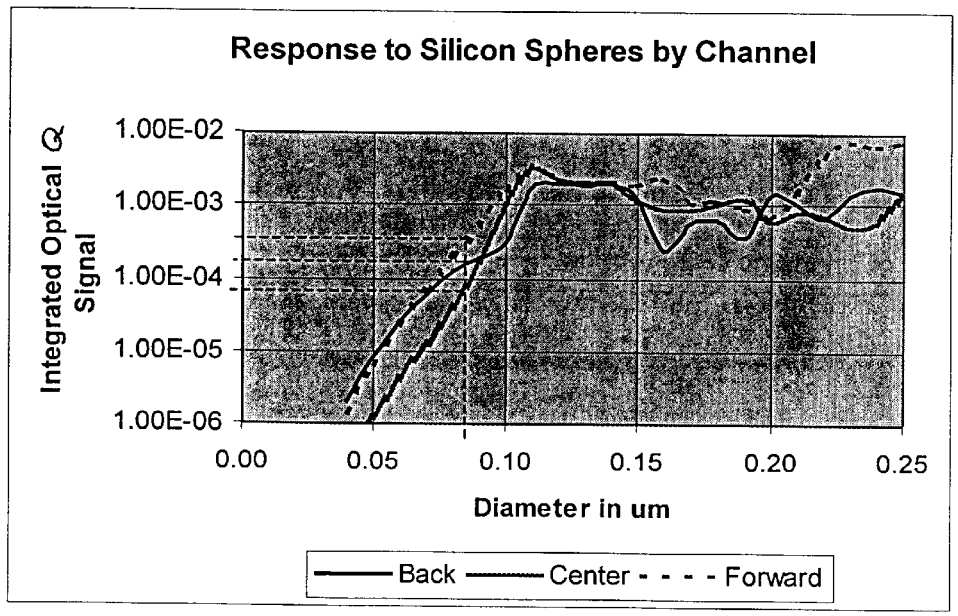
FIG. 4 is plot similar FIG. 3 for spherical silicon particles.
Figure 5:
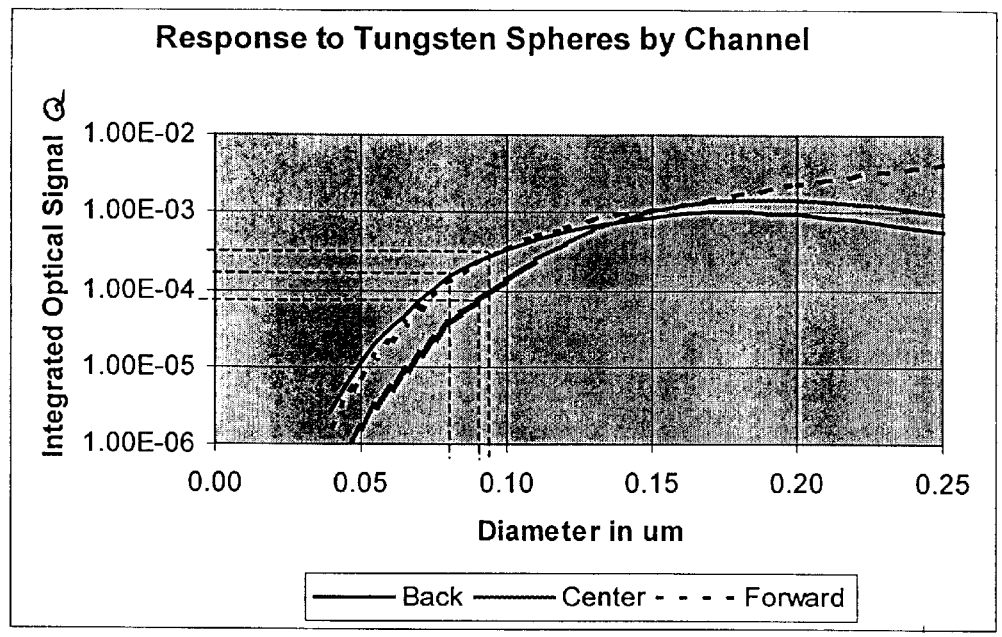
FIG. 5 is a plot similar to FIG. 3 for spherical tungsten particles.
Figure 6:
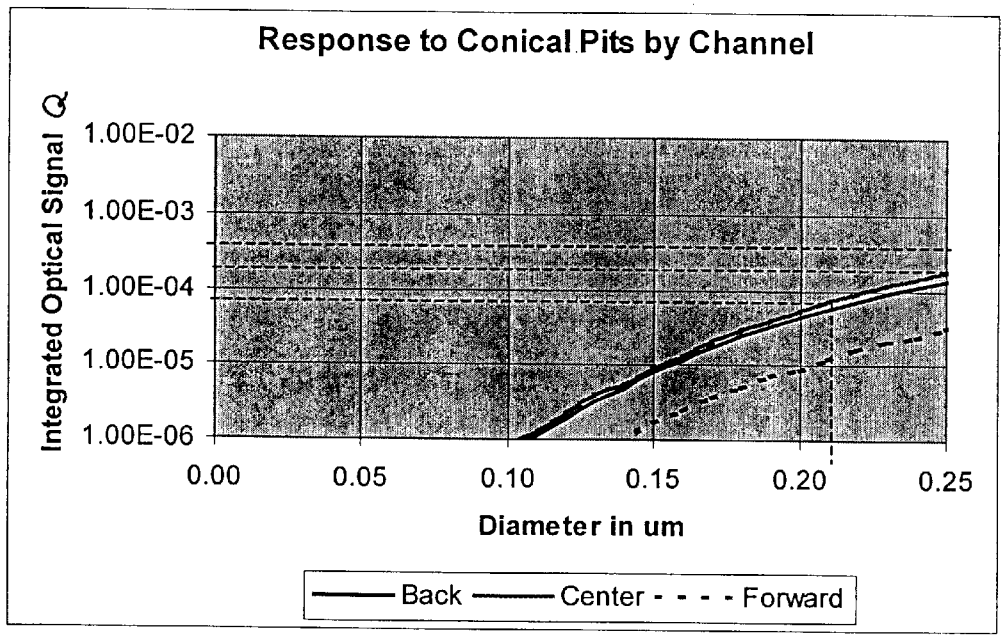
FIG. 6 is a plot similar to FIG. 3 for conical pits in the surface.
Figure 7:
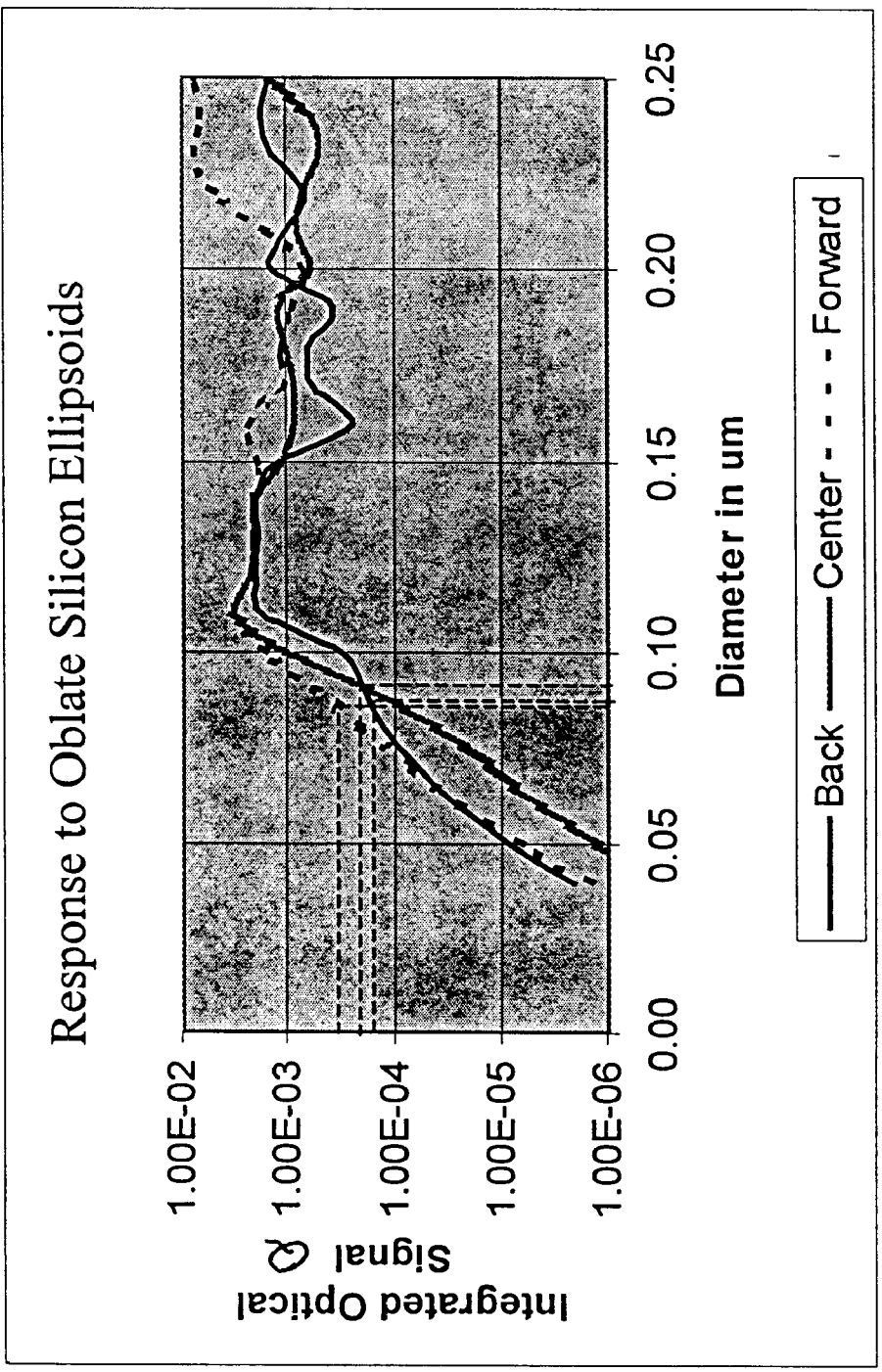
FIG. 7 is a plot similar to FIG. 3 for silicon particles having an oblate ellipsoid shape.

FIGS. 3 through 7 depict the types of data that can be stored in the data storage unit 54. FIG. 3 shows a plot of signal magnitude S versus diameter d for each of the back, center, and forward collectors for spherical particles of polystyrene latex. FIG. 4 shows a similar plot for spherical particles of silicon. FIG. 5 shows a similar plot for spherical particles of tungsten. FIG. 6 is a similar plot for conical pits, and FIG. 7 is a plot for silicon particles having an oblate ellipsoid shape. Each of these figures thus represents a different idealized defect type. Of course, these figures represent only some of the possible defect types that can occur on or in the substrate surface, and different or additional defect types (e.g., micro scratches, mounds, protrusions of various shapes, etc.) could be defined and plots similar to those in FIGS. 3–7 could be constructed for each of these defect types. Once all of the idealized defect types that are to be included in the database are defined, information such as that shown in FIGS. 3–7 is provided for each defect type and is stored in the data storage unit 54. This information can be provided either analytically by using scattering models, or empirically by actually testing the various defect types. Thus, the data storage unit stores a plurality M of databases corresponding to the M different defect types that are defined.

In accordance with the present invention, each of the M different databases contains a relationship between light collector signal magnitude S versus defect size d for each of a plurality N of different test configurations of the testing apparatus. For instance, in FIGS. 3–7, each of the three light collectors represents a different test configuration, such that N=3. The type of defect to which a given defect occurring at the substrate surface belongs is determined by running the apparatus in each of these different test configurations and obtaining the signal magnitudes from the light collection system 40 for each configuration, and comparing the signal magnitudes with the various S versus d relationships in the database. The idealized defect type whose data most closely matches the test data is identified as the most likely type for the defect on the substrate.

As an example, consider a spherical silicon particle on the substrate surface. When the particle is impinged by the incident light beam, each of the back, center, and forward light collectors produces a signal magnitude S. When these signal magnitudes are used with the corresponding curves in FIG. 4 for spherical silicon particles, each curve indicates the same particle diameter. However, if the same signal magnitudes are used with the curves for other defect types such as those in FIGS. 3 and 5–7, each curve in general will indicate a somewhat different defect size d as shown by the dashed lines in these figures. Accordingly, the invention employs a technique for determining how much variance or deviation there is between the defect sizes inferred for the various test configurations, and the defect type having the smallest deviation is identified as the most likely type to which the defect being analyzed belongs.

Various techniques for determining a deviation can be used in accordance with the invention. In a preferred embodiment of the invention, the measured signal magnitudes $S_1$ through $S_N$ corresponding to the N different test configurations are used with the S versus d relationships for each idealized defect type to determine an average defect size $<d>$. This average defect size is then used to determine corresponding signal magnitudes $<S_1>$ through $<S_N>$ that would be produced by a defect having the average size $<d>$. These determined signal magnitudes in general will differ from the actual measured signal magnitudes $S_1$ through $S_N$, and the degree of difference is an indication of how likely it is that the defect in question is of the particular idealized type. Thus, in accordance with the invention, a deviation parameter $\sigma$ is calculated as a combined deviation between the measured signal magnitudes $S_1$ through $S_N$ and the corresponding determined signal magnitudes $<S_1>$ through $<S_N>$ based on the calculated average defect size $<d>$. The idealized defect type yielding the smallest deviation parameter $\sigma$ is identified as the most likely type to which a defect in question belongs.

Preferably, the average defect size $<d>$ for a given defect type can be calculated as a weighted average based on the signal magnitudes, such as by the following formula:

$$<d> = \frac{(S_1)^\alpha d_1 + (S_2)^\alpha d_2 + \ldots + (S_N)^\alpha d_N}{(S_1)^\alpha + (S_2)^\alpha + \ldots + (S_N)^\alpha}$$

where the diameter $d_n$ for each nth test configuration (n=1 to N) is determined by using the signal magnitude $S_n$ measured with that test configuration and the S versus d relationship for that test configuration. The parameter $\alpha$ is a constant. Using different values for $\alpha$ allows the average size to be calculated in different ways. If $\alpha=0$ is chosen, then the average size $<d>$ is just the simple arithmetic average; however, using $\alpha=1$ is a more preferred approach that has yielded better accuracy for a number of defect types.

The deviation parameter for each defect type preferably is calculated based on a summation of differences between each measured signal magnitude S and the corresponding determined signal magnitude $<S>$ that corresponds to the average defect size $<d>$. For instance, the deviation parameter $\sigma$ can be calculated based on the formula:

$$\sigma = [|(<S_1> - S_1)|^\beta + |(<S_2> - S_2)|^\beta + \ldots + |(<S_N> - S_N)|^\beta]^{\frac{1}{\beta}}$$

The parameter $\beta$ is a constant. Using different values for $\beta$ allows the deviation parameter to be found in different ways. If $\beta=1$ is chosen, then the deviation parameter is the sum of the absolute values of the differences between the signals that were measured and the signals associated with the average size parameter $<d>$. A preferred value for $\beta$, however, is 2, such that the deviation parameter is the square root of the sum of the squares of the differences. This approach has yielded better accuracy for a number of defect types. Of course, it will be recognized that there are other ways in which a deviation parameter could be calculated in accordance with the invention, and the invention is not limited to any particular formula.

Once the deviation parameters $\sigma_1$ to $\sigma_M$ corresponding to the M different idealized defect types have been calculated, preferably, several of the smallest deviation parameters are identified and, for each of these deviation parameters, a relative probability value P is calculated, representing a relative probability that the defect in question belongs to the defect type associated with the particular deviation parameter. For example, if the three smallest deviation parameters are denoted $\sigma_1$, $\sigma_2$, and $\sigma_3$, a probability value for $\sigma_1$ is calculated based on the formula:

$$P_1 = \frac{(1/\sigma_1)^\delta}{(1/\sigma_1)^\delta + (1/\sigma_2)^\delta + (1/\sigma_3)^\delta}$$

Probability parameters $P_2$ and $P_3$ would be calculated by analogous formulas. The parameter $\delta$ is a constant. Using different values for $\delta$ allows the relative probability to be found in different ways. It has been found for many defect types that $\delta=1$ works well. However, other values for $\delta$ can be used instead, and indeed an entirely different formula could be used for deriving a probability parameter in accordance with the invention. Preferably, for each defect type corresponding to the three smallest deviation parameters, the defect type, probability value, and defect size are reported.

It will be noted with respect to FIGS. 4 and 7 for silicon particles that the signal magnitude versus diameter tends to include "dips" such that the S versus d relationship can have more than one diameter value for a given signal magnitude. This characteristic can cause problems in the data analysis of many optical defect scanners currently being used. However, in accordance with the present invention, these characteristic dips do not cause problems and can actually help in the identification of defect types. To handle any S versus d curve that yields multiple diameters for a given signal magnitude, each of the diameters is simply treated as if it were derived from another test configuration. Thus, a corresponding average defect size is calculated, and a deviation parameter is calculated, for each such diameter value. If more than one of the S versus d curves for a given defect type is multiple-valued in diameter, all of the combinations of the various diameters indicated by these curves are used. For instance, if three curves indicate three diameters each, there will be 27 different combinations of these diameters. Each combination is treated as a separate test configuration and a deviation parameter is calculated for each. In other respects, the method is the same as has been described above.

In the exemplary apparatus 20 and data analysis method described above, the various test configurations are produced by using a plurality of light collectors such that each collector represents a separate test configuration. However, different or additional test configurations can be provided in other ways. For instance, the polarization of the incident light beam can be varied (e.g., P-polarization and S-polarization) and/or the wavelength of the incident light beam can be varied. Alternatively or additionally, the polarization of the light collected and analyzed by the light collector system can be varied. Furthermore, additional or different light collectors can be employed, such as a collector for collecting specularly reflected light.

Although the examples described above employ three different test configurations as a result of having three light collectors, alternatively as few as two different test configurations could be used in accordance with the invention. For example, two different collectors could be used for separately collecting near-normal scattered light and more obliquely scattered light; these collectors, if desired, could be configured to collect light from a full 360° about the normal to the substrate surface. In this case, the database would include a different S versus d relationship for each of these two collectors and for each idealized defect type.

The invention thus provides a method and apparatus for not only determining the sizes of defects occurring at the surface of the substrate, but for also identifying various types of defects such as particles, pits, scratches, mounds on the surface, protrusions from the surface, the material of which a particle is made, the shape (e.g., spherical, ellipsoidal, etc.) of particles, and any other defect characteristic that produces discernable differences in the behavior of light scattered by the defect of interest. The method of the invention is applicable to optical scanners having any configuration of light collectors.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for classifying defects occurring at or near a surface of a smooth substrate, comprising:
   (a) defining a plurality M of different idealized types of defects that can occur at the surface of the substrate, such that a given defect occurring at the surface can be described at least approximately by a size parameter d and by one of said idealized types;
   (b) providing a database containing a plurality N of different sets of data for each said idealized type of defect, each set of data comprising a magnitude S of a signal from a light collector versus size parameter, the N different sets for each defect type corresponding to N different predetermined test configurations in which a beam of light having predetermined characteristics is impinged on the surface of the substrate at a predetermined incident angle and light emanating from the surface is collected by the light collector at a predetermined location above the surface and the intensity of the collected light is measured, the different predetermined test configurations being the same for each idealized defect type;
   (c) testing the substrate with each of said N different predetermined test configurations so as to derive N signal magnitudes $S_1$ to $S_N$ for a defect to be sized and classified;
   (d) for each of the M idealized defect types, using the database therefor to determine a plurality of sizes $d_1$ to $d_N$ corresponding to the N signal magnitudes $S_1$ to $S_N$; and
   (e) classifying the defect as being of the idealized type having the smallest spread between said plurality of sizes $d_1$ to $d_N$ and determining a size of the defect based on an average of said sizes.

2. The method of claim 1, wherein the plurality of idealized defect types include at least particles of a plurality of different materials.

3. The method of claim 1, wherein the plurality of idealized defect types include at least particles and pits.

4. The method of claim 1, wherein the plurality of different test configurations are defined by light collectors positioned at a plurality of different spaced locations above the surface of the substrate.

5. The method of claim 1, wherein the plurality of different test configurations are defined by a plurality of incident light beams having different incident angles relative to the surface of the substrate.

6. The method of claim 1, wherein the plurality of different test configurations are defined by a plurality of incident light beams having different polarizations.

7. The method of claim 1, wherein the plurality of different test configurations are defined by a plurality of incident light beams having different wavelengths.

8. The method of claim 1, wherein for any S versus d relationship in the database that has more than one size parameter d for a given signal magnitude S, each said size parameter d corresponding to the signal magnitude S is compared with the size parameters corresponding to the other signal magnitudes and the spread between the size parameters is determined and compared with the spreads for the other idealized defect types.

9. A method for classifying defects occurring at or near a surface of a smooth substrate, comprising:
   (a) defining a plurality M of different idealized types of defects that can occur at the surface of the substrate, such that a given defect occurring at the surface can be described at least approximately by a size parameter d and by one of said M idealized types;
   (b) providing a database containing a plurality N of different sets of data for each said idealized type of defect, each set of data comprising a magnitude S of a signal from a light collector versus size parameter, the N different sets for each defect type corresponding to N different predetermined test configurations in which a beam of light having predetermined characteristics is impinged on the surface of the substrate at a predetermined incident angle and light emanating from the surface is collected by the light collector at a predetermined location above the surface and the intensity of the collected light is measured, the different predetermined test configurations being the same for each idealized defect type;
   (c) testing the substrate with each of said N different predetermined test configurations so as to derive N signal magnitudes $S_1$ to $S_N$ for a defect to be sized and classified;
   (d) for each idealized defect type, using the database to determine at least N sizes $d_1$ to $d_N$ corresponding to the N signal magnitudes $S_1$ to $S_N$, calculating an average size $<d>$, and using the database to determine signal magnitudes $<S_1>$ to $<S_N>$ that correspond to the average size $<d>$;

(e) for each idealized defect type, calculating a deviation parameter σ representing a combined deviation between the signal magnitudes $S_1$ to $S_N$ and the determined signal magnitudes $<S_1>$ to $<S_N>$, so as to derive M deviation parameters $\sigma_1$ to $\sigma_M$ corresponding to the M idealized defect types; and (f) classifying the defect as being of the idealized type having the smallest deviation parameter σ, and determining a size of the defect based on the average size $<d>$ corresponding to said idealized type.

10. The method of claim 9, wherein the plurality of idealized defect types include at least particles of a plurality of different materials.

11. The method of claim 9, wherein the plurality of idealized defect types include at least particles and pits.

12. The method of claim 9, wherein the plurality of different test configurations are defined by light collectors positioned at a plurality of different spaced locations above the surface of the substrate.

13. The method of claim 9, wherein the plurality of different test configurations are defined by a plurality of incident light beams having different incident angles relative to the surface of the substrate.

14. The method of claim 9, wherein the plurality of different test configurations are defined by a plurality of incident light beams having different polarizations.

15. The method of claim 9, wherein the plurality of different test configurations are defined by a plurality of incident light beams having different wavelengths.

16. The method of claim 9, further comprising calculating a probability parameter associated with each of a plurality of the idealized defect types indicative of a relative probability that the defect belongs to the idealized defect type.

17. The method of claim 16, wherein the probability parameter for each idealized defect type is calculated based on the deviation parameters.

18. The method of claim 16, wherein probability parameters are calculated for only those idealized defect types having the J smallest deviation parameters, where J is an integer smaller than M.

19. The method of claim 9, wherein the deviation parameter for each idealized defect type is calculated based on a summation of deviations between each measured signal magnitude $S_n$ and the corresponding determined signal magnitude $<S_n>$, where n=1 to N.

20. The method of claim 9, wherein for any S versus d relationship in the database that has more than one size parameter d for a given signal magnitude S, each said size parameter d corresponding to the signal magnitude S is combined with the size parameters corresponding to the other signal magnitudes to form an average size parameter and said average size parameter is used to determine corresponding signal magnitudes $<S_1>$ to $<S_N>$ and a deviation parameter σ.

21. The method of claim 9, wherein the average size parameter $<d>$ for each idealized defect type is calculated as a weighted average in which each individual size parameter d is weighted by the signal magnitude S corresponding thereto.

22. The method of claim 9, wherein the database is provided by using a mathematical model to calculate signal magnitude versus size parameter for each test configuration and each idealized defect type.

23. The method of claim 9, wherein the database is provided by conducting a test for each test configuration and each idealized defect type.

24. A method for determining the material of which a particle occurring on a surface of a smooth substrate is made and for determining a size of the particle, comprising:

(a) defining a plurality of different materials of which the particle could be made;

(b) providing a database containing a group of N different sets of data for each said material, each set of data comprising a magnitude S of a signal from a light collector versus a particle diameter d, the N different sets for each material corresponding to N different predetermined test configurations in which a beam of light having predetermined characteristics is impinged on the surface of the substrate at a predetermined incident angle and light emanating from the surface is collected by the light collector at a predetermined location above the surface and the intensity of the collected light is measured, the different predetermined test configurations being the same for each material;

(c) testing the substrate with each of said N different predetermined test configurations so as to measure N signal magnitudes $S_1$ to $S_N$ for a particle to be identified and sized;

(d) comparing the measured signal magnitudes $S_1$ to $S_N$ with the database and identifying the material of the particle based on the group whose data most closely matches the measured signal magnitudes $S_1$ to $S_N$; and (e) determining the size of the particle based on the group identified in step (d).

25. The method of claim 24, wherein steps (d) and (e) comprise:

(1) for each material, using the corresponding group in the database to determine a plurality of sizes $d_1$ to $d_N$ corresponding to the N measured signal magnitudes $S_1$ to $S_N$, calculating an average size $<d>$, and using the database to determine signal magnitudes $<S_1>$ to $<S_N>$ that correspond to the average size $<d>$;

(2) for each material, calculating a deviation parameter σ representing a combined deviation between the measured signal magnitudes $S_1$ to $S_N$ and the determined signal magnitudes $<S_1>$ to $<S_N>$, so as to derive a plurality of deviation parameters $\sigma_1$ to $\sigma_N$ corresponding to the plurality of materials; and (3) classifying the defect as being of the material having the smallest deviation parameter σ, and determining a size of the defect based on the average size $<d>$ corresponding to said material.

26. The method of claim 25, wherein the deviation parameter for each idealized defect type is calculated based on the formula:

$$\sigma = [|(<S_1> - S_1)|^\beta + |(<S_2> - S_2)|^\beta + \ldots + |(<S_N> - S_N)|^\beta]^{\frac{1}{\beta}}.$$

27. An apparatus for determining the material of which a particle occurring on a surface of a smooth substrate is made and for determining a size of the particle, comprising:

a light source operable to create a light beam and impinge the light beam on the surface of the substrate with a predetermined incident angle relative to the surface and with a predetermined wavelength and predetermined polarization;

a light collector system disposed above the surface of the substrate and operable to collect, at one or more locations, light emanating from a particle on the surface as a result of the impingement of the light beam thereon and further operable to create a signal for each said location having a magnitude indicative of intensity of the collected light, the light collector system defining a separate channel for carrying the signal associated with each said location;

means for changing a test configuration of the apparatus so as to define a plurality N of different predetermined test configurations that, when tested, yield N measured signal magnitudes $S_1$ to $S_N$ for a particle to be identified and sized; and a storage medium storing a database containing a group of N different sets of data for each of a plurality M of predetermined materials of which the particle could be made, each set of data comprising a magnitude S of a signal versus a particle diameter d, the N different sets for each material corresponding to the N different predetermined test configurations.

28. The apparatus of claim 27, further comprising:

a computer connected with the storage medium and the light collector system and operable to compare the measured signal magnitudes $S_1$ to $S_N$ with the database and identify the material of the particle based on the group whose data sets most closely match the measured signal magnitudes $S_1$ to $S_N$ and operable to determine the size of the particle based on said group.

29. The apparatus of claim 28, wherein the computer is further operable to access each group in the database corresponding to each material and to determine, based on the data sets in each group, a plurality of sizes $d_1$ to $d_N$ for each material corresponding to the N measured signal magnitudes $S_1$ to $S_N$, calculate an average size <d> for each material, and determine signal magnitudes <$S_1$> to <$S_N$> that correspond to the average size <d> for each material.

30. The apparatus of claim 29, wherein the computer is further operable to calculate a deviation parameter σ for each material representing a combined deviation between the measured signal magnitudes $S_1$ to $S_N$ and the determined signal magnitudes <$S_1$> to <$S_N$> for each material so as to derive a plurality of deviation parameters $\sigma_1$ to $\sigma_M$ corresponding to the plurality M of materials, the computer being operable to identify the material of the particle based on the magnitudes of the deviation parameters.

31. The apparatus of claim 30, wherein the computer calculates the deviation parameter σ for each material based on a summation of deviations between each measured signal magnitude $S_n$ and the corresponding determined signal magnitude <$S_n$>, where n=1 to N.

32. The apparatus of claim 27, wherein the means for changing the test configuration comprises a plurality of light collectors of the light collector system, the light collectors being distributed at a plurality of locations above the surface of the substrate, each light collector serving to define a separate test configuration.

33. The apparatus of claim 27, wherein the means for changing the test configuration comprises means for changing the incident angle of the light beam.

34. The apparatus of claim 27, wherein the means for changing the test configuration comprises means for changing a polarization of the light beam.

35. The apparatus of claim 27, wherein the means for changing the test configuration comprises means for changing a wavelength of the light beam.

36. The apparatus of claim 27, wherein the means for changing the test configuration comprises means for changing a polarization of the light collected by the light collector system.

37. The apparatus of claim 27, further comprising a scanning system operable to effect relative movement between the light beam and substrate so as to scan the light beam over the surface.

38. An apparatus for classifying defects occurring at or near a surface of a smooth substrate, comprising:

a light source operable to create a light beam and impinge the light beam on the surface of the substrate with a predetermined incident angle relative to the surface and with a predetermined wavelength and predetermined polarization;

a light collector system disposed above the surface of the substrate and operable to collect, at one or more locations, light emanating from a defect on the surface as a result of the impingement of the light beam thereon and further operable to create a signal having a magnitude indicative of intensity of the collected light for each said location, the light collector system defining a separate channel for carrying the signal associated with each said location;

means for changing a test configuration of the apparatus so as to define a plurality N of different predetermined test configurations that, when tested, yield N measured signal magnitudes $S_1$ to $S_N$ for a defect to be identified and sized;

a storage medium storing a database containing a group of N different sets of data for each of a plurality M of predetermined idealized defect types that can occur at the surface of the substrate, each set of data comprising a magnitude S of a signal versus a defect size parameter d, the N different sets for each idealized defect type corresponding to the N different predetermined test configurations; and a computer connected with the storage medium and light collector system and operable to access each group in the database corresponding to each idealized defect type and to determine, based on the data sets in each group, a plurality of sizes $d_1$ to $d_N$ for each idealized defect type corresponding to the N measured signal magnitudes $S_1$ to $S_N$, calculate an average size <d> for each idealized defect type, and determine signal magnitudes <$S_1$> to <$S_N$> that correspond to the average size <d> for each idealized defect type.

39. The apparatus of claim 38, wherein the computer is operable to compare the measured signal magnitudes $S_1$ to $S_N$ with the database and identify the type of the defect based on the group whose data sets most closely match the measured signal magnitudes $S_1$ to $S_N$ and is operable to determine the size of the particle based on said group.

40. The apparatus of claim 39, wherein the computer is further operable to calculate a deviation parameter σ for each idealized defect type representing a combined deviation between the measured signal magnitudes $S_1$ to $S_N$ and the determined signal magnitudes <$S_1$> to <$S_N$> for each idealized defect type so as to derive a plurality of deviation parameters $\sigma_1$ to $\sigma_M$ corresponding to the plurality of idealized defect types, the computer being operable to identify the type of the defect based on the magnitudes of the deviation parameters.

41. The apparatus of claim 38, further comprising means for processing the signals from the light collector system so as to create the measured signal magnitudes $S_1$ to $S_N$.

* * * * *

UNITED STATES PATENT AND TRADEMARK OFFICE
CERTIFICATE OF CORRECTION

PATENT NO. : 6,760,100 B2 Page 1 of 1
DATED : July 6, 2004
INVENTOR(S) : Ivakhnenko et al.

It is certified that error appears in the above-identified patent and that said Letters Patent is hereby corrected as shown below:

Title page,
Item [56], References Cited, U.S. PATENT DOCUMENTS, insert the following:
-- 6,091,493    7/2000        Stover et al.
   6,122,047    9/2000        Stover et al.
   6,169,601    1/2001        Eremin et al. --
FOREIGN PATENT DOCUMENTS, insert the following:
-- WO 98/25131        6/1998        WIPO --.

Signed and Sealed this

Ninth Day of November, 2004

JON W. DUDAS
*Director of the United States Patent and Trademark Office*